United States Patent [19]

Christensen et al.

[11] Patent Number: Plant 5,398

[45] Date of Patent: Jan. 29, 1985

[54] ROSE PLANT CV. AROWEDYE

[75] Inventors: Jack E. Christensen; Herbert C. Swim, both of Ontario, Calif.

[73] Assignee: Armstrong Nurseries, Inc., Ontario, Calif.

[21] Appl. No.: 503,046

[22] Filed: Jun. 10, 1983

[51] Int. Cl.[3] ..... A01H 5/00

[52] U.S. Cl. ..... Plt./11

[58] Field of Search ..... Plt./11

*Primary Examiner*—Robert E. Bagwill

*Attorney, Agent, or Firm*—Synnestvedt & Lechner

[57] ABSTRACT

A new variety of rose plant of the Hybrid Tea class, being a half-hardy, outdoor, tall bush seedling, particularly adapted for garden decoration and which produces large pointed buds and large, slow-opening, long-lasting blooms on long, strong cutting stems. In contrast to other yellow roses, its clear yellow coloration lasts well throughout the life of the bloom.

1 Drawing Figure

1

This invention relates to a new class of Hybrid Tea rose. The plant is a seedling of the half-hardy, tall bushy outdoor type, cultivated for garden decoration. References to the growth and behavior of the plant pertain to plants raised in Southern California.

The new variety was hybridized by Herbert C. Swim and Jack E. Christensen in Ontario, Calif. by crossing an undisseminated seedling of Granada×Garden Party as the seed parent with an undisseminated seedling of Bewitched×King's Ransom as the pollen parent. It holds its distinguishing characteristics through succeeding propagations by budding.

The new variety usually bears its flowers singly, but sometimes two to three blooms are carried on one stem, in regular flat clusters. The stems are strong and of medium to long length. The plant blooms abundantly outdoors, and nearly continuously during the growing season. It has a slight tea fragrance.

This new cultivar may most readily be distinguished in the following ways from its seed parent, (which itself is an unnamed, undisseminated seedling of Granada×-Garden Party) in that the seedling parent bears flowers of a light-yellow-blushed-soft-pink coloration, whereas the new rose bears flowers of significantly deeper yellow coloration essentially as described and illustrated herein. Further, the new rose bears long pointed buds whereas the seed parent bears distinctly ovoid buds.

This new cultivar may most readily be distinguished from its pollen parent, (an undisseminated seedling of Bewitched×King's Ransom) by the following combination of characteristics:

Whereas the pollen parent bears flowers a relatively uniform apricot-orange coloration, the new cultivar bears flowers of a yellow-blushed-pink combination essentially as described and illustrated herein.

The pollen parent bears flowers with 50 to 60 petals whereas the new rose bears flowers with significantly lower petalage (33 to 38).

The new rose bears long pointed buds, whereas the pollen parent bears significantly shorter, flatter, more avoid buds. Whereas the new cultivar produces a mediumtall bush with an upright spreading habit, the pollen parent yields a significantly taller bush with a very upright habit.

The accompanying drawing illustrates the plant in color and shows the flowering thereof from bud to full bloom.

2

Throughout this specification, color names beginning with a small letter signify that the name of that color, as used in common speech, is aptly descriptive. Color names beginning with a capital letter designate values based upon The R.H.S. Colour Chart, published by The Royal Horticultural Society in London, England.

BUD

The peduncle is average in length and average to heavy in caliper, being erect, stiff and moderately smooth, with numerous stipitate glands.

Before the calyx breaks, the bud is medium to large in size; of long, pointed ovoid form; with few foliaceous appendages and a few stipitate glands on the surface of the bud. Usually, slender foliaceous parts extend beyond the tip of the bud equal to one-forth or more of its length.

As the calyx breaks, the color is between Yellow 12B and Yellow-Orange 14C. The inner surface of the sepals carry a fine wooly tomentum. Margins of the sepals are lined with stipitate glands.

As the first petal opens, the bud is large in size and of long, pointed ovoid to urn-shaped form. The color on the outside of the petal is between Yellow 12B and Yellow-Orange 15B, areas exposed to sunlight sometimes blush to near Red 48A. The inside surface of the petal is the same as the outside surface but with no blushing. The bud opens up well, and is not prevented from opening by cold, hot, wet or dry weather.

BLOOM

The size of the bloom when fully open is from average to large, ranging from 4½ to 5½ inches. The petalage is double, with from 33 to 38 petals, plus from 1 to 8 petaloids; the petals are arranged regularly. The bloom is high centered to globular at first, becoming cupped to high centered. At first the petals remain tightly cupped, with tips reflexed outward, and become later at maturity loosely cupped, with tips reflexed outward.

The petals are thick; with inside slightly satiny and outside shiny to satiny. The outside petals are broadly obovate and the apex is sometimes notched. The intermediate petals are less broadly obovate and the apex is sometimes notched. The inside petals are narrowly obovate, irregular and the apex is sometimes notched.

The petal colors may be modified by being bordered or penciled or blotched, shaded and/or washed with other colors.

The description immediately following is of a newly opened flower of a plant grown outdoors in the month of August in Ontario, Calif.

The outside surface of outside, intermediate and inside petals was between Yellow-Orange 16B and Yellow 12B. The inner surface of the outside petals was between Yellow-Orange 16B and Yellow 12B and is sometimes lightly blushed with Red 54C. The inside surface of the intermediate and inner petals is of the same coloration as the inner surface of the outside petals but with less blushing.

The description which follows was made from a rose that was open for three days. It had been grown outdoors in the month of August, at Ontario, Calif.

The outer surface of the outside petals is between Yellow-Orange 16D and Yellow 12C.

The inner surface of the inside and outside petals was the same coloration as that of the outer surface of the outside and inside petals but is sometimes lightly blushed with near Red 54D.

The general color effect of the newly opened flower is between Yellow-Orange 16B and Yellow 12B and sometimes the outer petals are lightly blushed with near Red 54C. The bloom after being three days open, gives a general color effect of between Yellow-Orange 16D and Yellow 12C and sometimes the petal edges are blushed with near Red 54D. Petals drop off cleanly and are not particularly affected by cold, hot, wet or dry weather.

The flower on the bush in the garden persists from three to four days in the month of August. Cut roses grown outdoors and kept at living-room temperatures will last from four to five days in the month of August.

REPRODUCTIVE ORGANS

There are an average number of stamens arranged irregularly about the pistils.

Filaments are of short to medium-length and most are with anthers.

The anthers are of medium size and all opening approximately at once. When immature the color is near Yellow-Orange 14B and when mature the color is near Greyed-Orange 172A.

Pollen is moderately abundant and near Yellow-Orange 14C in color.

There are from few to an average number of pistils, being approximately 70 in number.

The styles are moderately uneven, of average length, thin in caliper, and somewhat loosely bunched.

The stigma is near Yellow 4C in color.

Usually most of the ovaries are enclosed in the calyx.

Normally this variety does not set hips under Ontario, Calif. growing conditions.

FOLIAGE

The compound leaves usually comprise from three to five leaflets. They are abundant, of medium size to large; and moderately heavy. The leaflets are oval, with apex acute and base acute. The margin is irregularly serrate.

The upper surface of the mature foliage is between Green 131A and Green 137A in color. The under surface is a color between Yellow-Green 148B and Greyed-Green 191A.

The young foliage has an upper surface which is between Greyed-Purple 187A and 187B. The under surface is between Greyed-Purple 187D.

The rachis is of average size, the upper side being grooved and with some stipitate glands on the edges. The underside is moderately smooth and with stipitate glands.

The stipules are of medium-length to long, medium-width, and with medium-length points turning out at an angle of less than 45°.

The plant displays a more than average resistance to mildew and blackspot when compared to other varieties grown under comparable conditions in the same locality.

GROWTH

The plant is bushy, of upright to spreading habit, and much branched. It displays vigorous growth. The canes are medium to heavy in caliper.

The main stems are between Yellow-Green 146D, and Yellow-Green 148C in color. They bear a few large prickles which are of short to medium-length, almost straight hooked slightly downward, with a moderately long broad base. The color is near Greyed-Yellow 161B. There are a few small prickles and no hairs; the small prickles are near Greyed-Yellow 161B in color.

The branches are between Yellow-Green 146B, and Yellow-Green 147A in color. They bear a few large prickles which are of short to medium-length, almost straight, hooked slightly downward, with moderately long broad base. The color is near Greyed-Orange 166A. There are very few small prickles and no hairs; the small prickles are near Greyed-Orange 166A in color.

New shoots have a color near Yellow-Green 146D, washed heavily with near Greyed-Purple 187D. There are from a few to several large prickles which are of short to medium-length almost straight but hooked slightly downward, with a moderately long, broad base. The color is near Greyed-Purple 185D. There are a few small prickles and no hairs; the small prickles are near Greyed-Purple 185D in color.

We claim:

1. A new and distinct variety of rose plant of the Hybrid Tea class, substantially as herein shown and described, being particularly characterized by large pointed buds that are usually produced singly on long strong stems; its clear yellow coloration lasts throughout the life of the bloom and longer than most other yellow roses; its large blooms open very slowly and are uniquely (for yellow rose cultivars) long-lasting in the garden and in the vase; it is significantly more vigorous than most other yellow roses and provides an attractive, easy-to-grow garden specimen; its flowering stems are long and low-thorned, and it has an abundance of large foliage during the growing season.

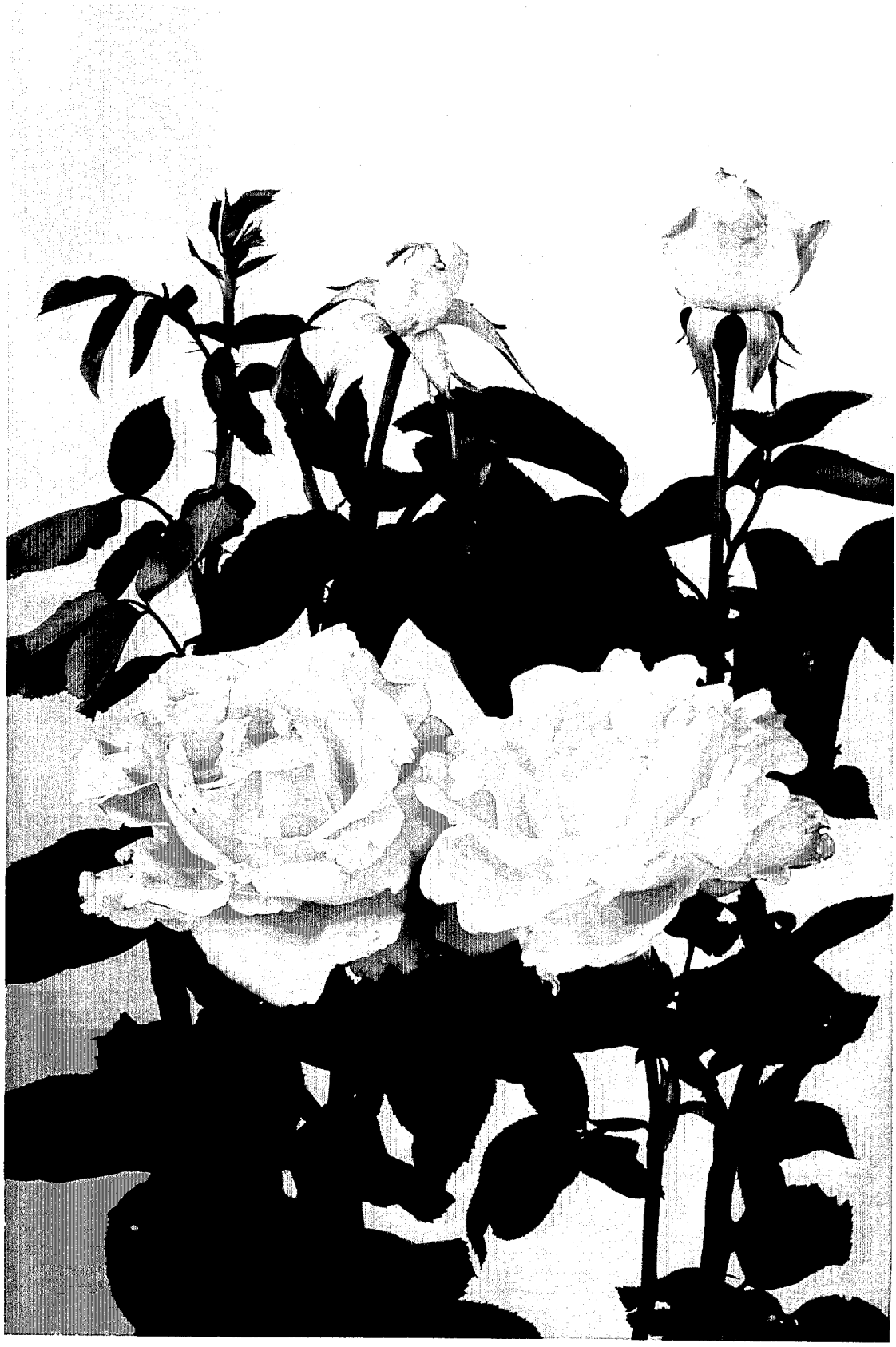

* * * * *